(12) United States Patent
Kumagai et al.

(10) Patent No.: US 12,736,553 B2
(45) Date of Patent: Sep. 15, 2026

(54) TESTING SYSTEM, STORAGE DEVICE, AND RACK STORAGE METHOD

(71) Applicant: SYSMEX CORPORATION, Kobe (JP)

(72) Inventors: Atsushi Kumagai, Kobe (JP); Yuji Wakamiya, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 673 days.

(21) Appl. No.: 16/913,112

(22) Filed: Jun. 26, 2020

(65) Prior Publication Data

US 2020/0408793 A1 Dec. 31, 2020

(30) Foreign Application Priority Data

Jun. 28, 2019 (JP) ................................ 2019-122304

(51) Int. Cl.
*G01N 35/02* (2006.01)
*G01N 33/49* (2006.01)
(Continued)

(52) U.S. Cl.
CPC ........... *G01N 35/021* (2013.01); *G01N 33/49* (2013.01); *G01N 33/5302* (2013.01);
(Continued)

(58) Field of Classification Search
CPC ................. G01N 35/021; G01N 33/49; G01N 33/5302; G01N 35/00584; G01N 35/04;
(Continued)

(56) References Cited

U.S. PATENT DOCUMENTS 6,117,392 A * 9/2000 Hanawa ........... G01N 35/00603 422/65
2006/0193754 A1* 8/2006 Toyoda ................ G01N 35/026 422/400
2006/0216199 A1* 9/2006 Koike ................. G01N 35/026 422/65

(Continued)

FOREIGN PATENT DOCUMENTS

CN 107407687 A 11/2017
CN 107430143 A 12/2017

(Continued)

OTHER PUBLICATIONS

Extended European search report issued on Mar. 22, 2021 in European patent application No. 20181933.1.

(Continued)

*Primary Examiner* — Benjamin R Whatley
*Assistant Examiner* — Curtis A Thompson
(74) *Attorney, Agent, or Firm* — Crowell & Moring LLP

(57) ABSTRACT

The invention allows a rack storage mode to be set in accordance with the situation in a facility. A testing system 1 includes a storage device 240 for storing a rack R holding containers A in which samples tested by the testing units 13 and 14 are accommodated, and the storage device 240 includes a table 130 capable of accommodating a plurality of racks R, a setting unit 230 for setting a first mode for starting storage of a plurality of racks R from a first end 130*a* of the table 130 and a second mode for starting storage of a plurality of racks R from a second end 130*b* of the table 130, and a moving device 102 for moving the rack R according to the mode set by the setting unit 230.

11 Claims, 16 Drawing Sheets

(51) Int. Cl.
*G01N 33/53* (2006.01)
*G01N 35/00* (2006.01)
*G01N 35/04* (2006.01)

(52) U.S. Cl.
CPC ....... *G01N 35/00584* (2013.01); *G01N 35/04* (2013.01); *G01N 2035/0412* (2013.01)

(58) Field of Classification Search
CPC .............. G01N 2035/0412; G01N 2035/0484; G01N 35/00; G01N 2035/00178; G01N 2035/00306; B01L 9/00
See application file for complete search history.

(56) References Cited

U.S. PATENT DOCUMENTS

| | | | | |
|---|---|---|---|---|
| 2007/0202011 | A1* | 8/2007 | Nogawa | G01N 35/026 422/65 |
| 2010/0166605 | A1* | 7/2010 | Hamada | G01N 35/026 422/65 |
| 2011/0076194 | A1 | 3/2011 | Kitagawa et al. | |
| 2014/0037502 | A1* | 2/2014 | Tatsutani | G01N 35/00584 422/67 |
| 2017/0285052 | A1 | 10/2017 | Tatsutani et al. | |
| 2018/0002108 | A1* | 1/2018 | Tatsutani | B65G 1/026 |
| 2018/0003729 | A1* | 1/2018 | Tatsutani | G01N 35/026 |

FOREIGN PATENT DOCUMENTS

| | | | |
|---|---|---|---|
| CN | 109675653 | A | 4/2019 |
| EP | 2299281 | A2 | 3/2011 |
| EP | 2423689 | A1 | 2/2012 |
| EP | 2724778 | A1 | 4/2014 |
| JP | 2009-036513 | A | 2/2009 |
| JP | 2010-151708 | A | 7/2010 |
| JP | 2011-074554 | A | 4/2011 |
| JP | 2012-112682 | A | 6/2012 |
| JP | 2019-085428 | A | 6/2019 |

OTHER PUBLICATIONS

Japanese Office Action with English Translation, dated Nov. 28, 2022, pp. 1-7, issued in Japanese patent application No. 2019-122304, Japan Patent Office, Chiyoda Tokyo, Japan.
The Communication pursuant to Article 94(3) EPC issued on Jun. 15, 2023 in a counterpart European patent application No. 20181933.1.
First Office Action Issued in Chinese Patent Application No. 202010563500.1 dated Jan. 24, 2025 (in English and Chinese) (25 pages).
Office Action issued in European Patent Application No. 20181933.1, dated Jan. 31, 2025 (7 pages).

* cited by examiner

Rear
Right
Front
Left
1
240
S1
S2
10
11
12
13
14
15
17
18
19
180
21
50
51
53
70
71
130a
130b
A
N
R
W Rear
Right
Left
Front
19
N
240
1
130b
130a
15
17
180
W
S1
S2
R
70
71
13
14
53
50
50b
50a

TESTING SYSTEM, STORAGE DEVICE, AND RACK STORAGE METHOD

RELATED APPLICATIONS

This application claims priority to Japanese Patent Application No. 2019-122304, filed on Jun. 28, 2019, the entire content of which is incorporated herein by reference.

BACKGROUND OF THE INVENTION

1. Field of the Invention

The present invention relates to a testing system, a storage device, and a rack storage method.

2. Description of the Related Art

A sample processing system disclosed in Japanese Patent Application Publication No. 2012-112682 is an example of a testing system that automatically performs a testing of a sample such as a blood coagulation analysis or an immune serum analysis. The sample processing system of Japanese Patent Application Publication No. 2012-112682 sequentially transports a rack holding a plurality of sample containers along a predetermined transport path, measures the samples in the containers in a measurement unit, and collects the rack in a storage unit.

SUMMARY OF THE INVENTION

There are various circumstances in a facility where a testing system is installed, and depending on the installation position of the testing system and the operations of the testing, a user may feel inconvenienced when removing a rack stored in the storage unit.

In view of the aforesaid problem, the present invention provides a testing system, a storage device, and a rack storage method capable of setting the storage of a rack according to the situation of a facility.

As shown in FIG. 1, the testing system (1) of one aspect of the present invention includes testing devices (testing units 13, 14) for testing a sample of a container (A) held in a rack (R), a transport device (transport unit 12) for transporting a rack (R) that holds a container (A) of a sample tested by a testing device (testing units 13 and 14), and a storage device (240) for storing a rack (R) transported by the transport device (transport unit 12). The storage device (240) includes storage unit (table 130) capable of storing a plurality of racks (R), a setting unit (see FIG. 7: 230) for setting a first mode for storing a plurality of racks (R) in the storage unit (table 130) in a first mode and a second mode for storing a plurality of racks in a second mode that is different from the first mode, and a moving unit for moving the rack (R) according to the mode set by the setting unit (see FIG. 7: 102).

According to this aspect, the mode of storing a plurality of racks can be set by the setting unit. In this way it is possible to set a suitable rack storage mode in the testing system according to the situation of the facility.

As shown in FIG. 16, the testing system (301) of another aspect of the invention includes a testing device (13, 14) for testing a sample in a container held in a rack, a storage device (340) for storing a rack holding a container of a sample tested by the testing device (13, 14), a transport device (12) for transporting a rack from the testing device (13, 14) to the storage device (340), a setting unit (230) for selecting a storage mode of a rack in the storage device (340), a moving unit (302) for moving the rack transported to the storage device (340) by the transport device (12) to the storage device (340), and a control unit (142) for controlling the moving unit (302) so as to store a rack in the storage device (340) by a first mode when the first mode is selected by the setting unit (230), and controlling the moving unit (302) so as to store a rack in the storage device (340) by a second mode when the second mode is selected by the setting unit (230).

According to this aspect, the mode of storing a plurality of racks can be set by the setting unit. In this way a suitable rack storage mode can be set according to the layout state of the testing device and the transport device in the testing system.

As shown in FIG. 1, the storage device (240) of another aspect of the invention includes is a storage device (240) for storing a rack (R) capable of holding a container (A), and includes storage unit (table 130) capable of storing a plurality of racks (R), a setting unit (see FIG. 7: 230) for setting a first mode for starting the storage of a plurality of racks (R) from a first reference position (first end part 130*a*) of the storage unit (table 130) and a second mode for starting the storage of a plurality of racks from a second reference position (second end part 130*b*) that is different form the first reference position (first end part 130*a*) of the storage unit (table 130), and a moving unit (see FIG. 7: 102) for moving the rack (R) according to the mode set by the setting unit.

According to this aspect, when the first mode is set by the setting unit, the housing of the plurality of racks is started from the first reference position in the storage unit. When the second mode is set by the setting unit, the storage of the plurality of racks is started from the second reference position in the storage unit. In this way it is possible to set the storage in the storage device so that the storage of the rack is started near the work position of the worker of the storage device.

As shown in FIG. 1, the storage method of another aspect of the invention is a method of storing a rack (R) capable of holding a container (A), and the method includes a step (see FIG. 8: B4, B5) of setting a first mode for starting the storage of a plurality of racks from a first reference position (first end 130*a*) of a storage unit (table 130) capable of storing the racks (R) side by side and a second mode for starting the storage of a plurality of racks from a second reference position (second end 130*b*) that is different from the first reference position (first end 130*a*) of the storage unit (table 130), and a step (see FIG. 12: C3 to C4, C5 to C9) of moving the rack (R) according to the set mode.

According to this aspect, the storage of the plurality of racks can be set to start from the first reference position or the second reference position by setting the mode. In this way it is possible to set the rack to be started from a position suitable for the operator to remove the rack.

The testing system, storage device, and rack storage method according to the present invention enables an operator to remove a stored rack appropriately regardless of the installation position and testing operation of the testing system.

DETAILED DESCRIPTION OF THE PREFERRED EMBODIMENTS

Figure 1:
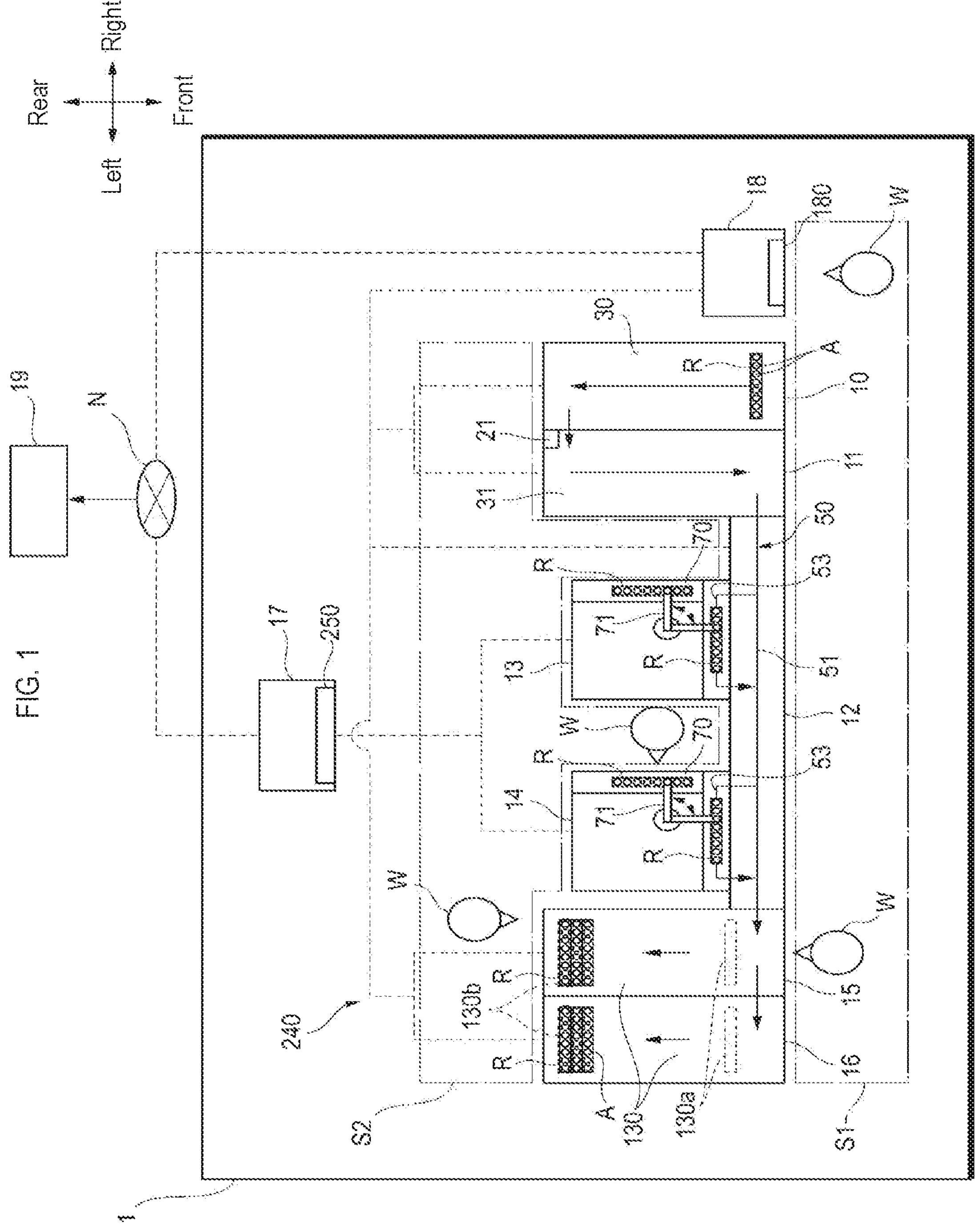
FIG. 1 is a schematic diagram showing a structural example of a testing system in a plan view.

Hereinafter, preferred embodiments of the present invention will be described with reference to the drawings. First, a testing system according to the present embodiment will be described. FIG. 1 shows a structural example of a testing system 1 in plan view. Areas S1 and S2 indicated by dotted lines in FIG. 1 are examples of a main work area of a worker W who is working in a room where the testing system 1 is installed. The work area S1 is an area facing one side of the testing system 1 when the testing system 1 is viewed in plan view, and the work area. S2 is an area facing the other side of the testing system L Hereinafter, the work area S1 side of the testing system 1 is referred to as “front”, and the work area S2 side of the testing system 1 is referred to as “rear”. The right side when the testing system 1 is viewed from the front side is defined as “right” of the testing system 1, and the left side when the testing system 1 is viewed from the front side is defined as “left” of the testing system 1.

The testing system 1 includes loading units 10 and 11, a transport unit 12, testing units 13 and 14, storage units 15 and 16, a first control unit 17, and a second control unit 18. In the present embodiment, a storage device 240 is configured by the storage units 15, 16, and the second control unit 18.

Figure 2:
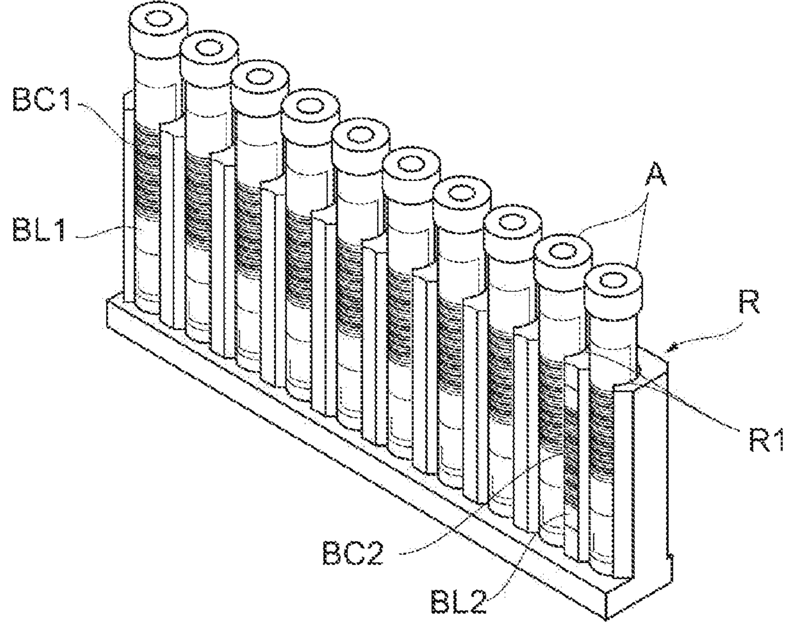
FIG. 2 is a perspective view showing an example of a rack.

A rack R holding a plurality of containers A containing samples is placed in the loading unit 10 by an operator. The loading unit 10 can arrange a plurality of racks R, and is configured each rack R can be sequentially transported to the loading unit 11. The rack R has a plurality of holding holes R1 arranged in a row as shown in FIG. 2, for example, and can hold a container A inserted in the holding hole R1. A barcode label BL1 is attached to the container A, and a barcode BC1 including the identification information of the container A is printed on the barcode label BL1. A barcode label BL2 is attached to the rack R, and a barcode BC2 including identification information of the rack R is printed on the barcode label BL2.

The loading unit 10 shown in FIG. 1 has a table 30 in which racks R can be arranged in a front-rear direction. The rack R is arranged on the table 30 in a direction in which the containers A are arranged side by side. The loading unit 10 moves the rack R disposed at the forefront of the table 30 to the rearmost part in the front-rear direction, and also moves the rack R to the left at the rearmost part, and moves the rack R to the loading unit 11 adjacent to the left side.

The loading unit 11 has a table 31 on which racks R can be arranged in the front-rear direction. The loading unit 11 can move the rack R carried to the rearmost position on the table 31 to the forefront position in the front-rear direction. The loading unit 11 also can move the rack R to the left at the forefront, and can unload the rack R to the transport unit 12 adjacent to the left side. The loading unit 11 includes a rack information reading unit 21 configured by a barcode reader. The rack information reading unit 21 is provided at the rearmost part of the loading unit 11 and reads the barcodes BC1 and BC2 shown in FIG. 2 from the rack R and the container A loaded in the loading unit 11 to acquire identification information of the rack R and the container A.

The transport unit 12 includes a transport path 50 for transporting the rack R received from the loading unit 11 to the storage unit 15 that is a predetermined distance on the left side from the loading unit 11. The transport path 50 includes a main transport path 51 and two testing paths 53. The main transport path 51 is formed in a long linear shape in the left-right direction, and can transport the rack R linearly from the loading unit 11 to the storage unit 15. The two testing paths 53 are respectively provided on the rear side of the main transport path 51, and transport the rack R of the main transport path 51 to the front of the testing unit 13 and the front of the testing unit 14. Each of the two testing paths 53 is configured to branch off from the main transport path 51, pass in front of the testing units 13 and 14, and return to the main transport path 51. The transport unit 12 can transport the rack R loaded from the loading unit 11 to the storage unit 15 on the left side of the main transport path 51 via one or both testing paths 53. The transport unit 12 is configured to stop the rack R in front of the testing units 13 and 14 on the testing path 53.

The testing units 13 and 14 are units for testing a sample, such as a blood coagulation analysis unit and a blood immunoassay unit. The testing units 13 and 14 have a rectangular outer shape in plan view, and are adjacent to the transport unit 12 behind the testing path 53. The sample of the container A held by each rack R transported to the testing path 53 by the transport unit 12 is tested by either the testing unit 13 or the testing unit 14 or both. The testing units 13 and 14 include a rack setting unit 70 and a sample extraction arm 71. The rack setting unit 70 is provided on the right side of the testing units 13 and 14, and allows the operator to directly set the rack R. The sample extraction arm 71 is configured to access each of the containers A of the rack R of the rack setting unit 70 and the container A of the rack R stopped on the testing path 53. The sample extraction arm 71 extracts a sample from the container A for examination and introduces the sample into the testing units 13 and 14.

The storage units 15 and 16 are units for storing the rack R loaded from the transport unit 12. Each rack R loaded in from the transport unit 12 is stored in one of the storage units 15 and 16, The storage units 15 and 16 have a long shape in the front-rear direction, and include a table (storage unit) 130 in which the racks R can be arranged in the front-rear direction, such that a rack R loaded to the forefront can be transported onto the table 130 for storage. The storage units 15 and 16 start storing a plurality of racks from the first end (first reference position) 130*a* on the front side of the table 130, and can store a maximum of 25 racks R in the table 130. The storage units 15 and 16 start storing a plurality of racks R from the second end (second reference position) 130*b* on the rear side of the table 130, and also can store a maximum of 25 racks R in the table 130.

The first control unit 17 is a computer that is connected to the testing units 13 and 14; the first control unit 17 manages information related to sample testing, and controls the operation of the testing units 13 and 14. The first control unit 17 also is communicably connected to the second control unit 18 and the host computer 19 via the in-facility network N.

The display unit 250 is a display that is connected to the first control unit 17, and displays information related to the sample testing and information related to the operation of the testing units 13 and 14.

The second control unit 18 is disposed on the right side of the carry-in unit 10 and is connected to the carry-in units 10, 11, the transport unit 12, and the storage units 15, 16 by a dedicated line; the second control unit 18 is a computer for managing the transport state of the rack R and controlling the transport destination of the rack R The display unit 180 is a display that is connected to the second control unit 18 and displays a setting screen for the storage units 15 and 16 of the testing system 1.

Figure 3:
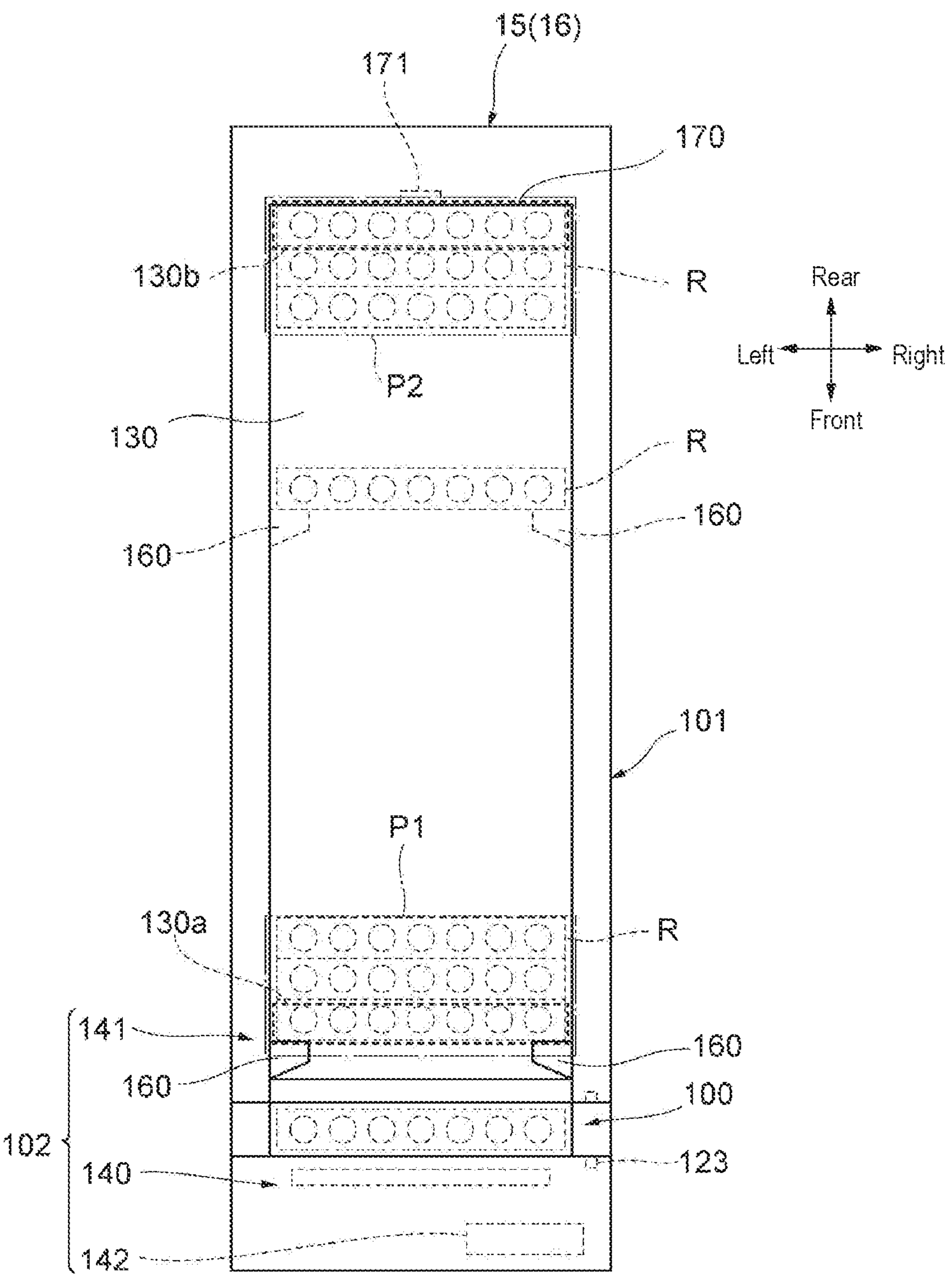
FIG. 3 is a schematic diagram showing an example of a storage unit in a plan view.

FIG. 3 is a schematic diagram showing the storage units 15 and 16 in a plan view. Each of the storage units 15 and 16 includes a loading unit 100 into which the racks R are loaded, a table 130 capable of storing up to 25 racks R, and a moving unit 102 for moving the racks R loaded into the loading unit 100 to the table 130.

The loading unit 100 is provided on the front side of the storage units 15 and 16. The loading unit 100 is located on an extension of the main transport path 51 of the transport unit 12, and the rack R is loaded in a direction in which the containers A are lined up in the left-right direction. The loading unit 100 has a width in the front-rear direction and a length in the left-right direction such that one rack R can be loaded. The loading unit 100 is provided with a sensor 123 that detects that the rack R has been loaded. The sensor 123 is an infrared sensor.

Figure 4:
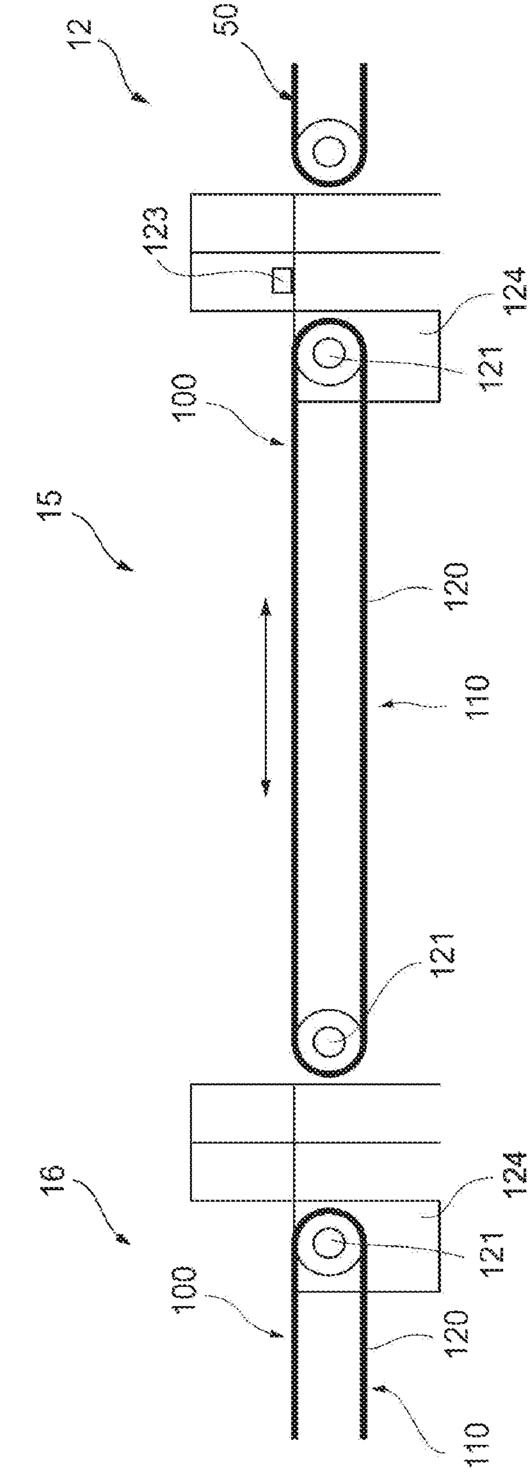
FIG. 4 is an explanatory diagram showing a structural example of a loading unit.

The loading unit 100 has a belt conveyor 110 as shown in FIG. 4. The belt conveyor 110 has two rollers 121 arranged side by side in the left-right direction, a belt 120 looped between the two rollers 121, and a drive source 124 connected to the rollers 121. The two rollers 121 are rotated by the drive source 124. The belt 120 is rotated by a roller 121. The loading unit 100 can receive the rack R from the transport path 50 of the transport unit 12 by rotating the belt 120 via the drive source 124, and can move the rack R to the center of the loading unit 100 in the left-right direction. The loading unit 100 of the storage unit 15 can also move the rack R to the loading unit 100 of the storage unit 16 adjacent to the left side.

As shown in FIG. 3, the table 130 is provided on the rear side of the storage units 15 and 16 in a plan view, and is adjacent to the rear side of the loading unit 100. The table 130 is formed by a rectangular horizontal plate that is long in the front-rear direction. On the table 130, a maximum of 25 racks R in which the containers A are arranged in the horizontal direction can be stored side by side. Note that the table 130 has a length of 50 cm or more in the front-rear direction.

The moving unit 102 includes a first transport mechanism 140, a second transport mechanism 141, and a control unit 142. The first transport mechanism 140 moves the rack R of the loading unit 100 rearward toward the first end (first reference position) 130*a* on the front side of the table 130. The second transport mechanism 141 moves the rack R on the table 130 rearward toward the second end (second reference position) 130*b* on the rear side of the table 130. The control unit 142 is set to the first mode or the second mode in response to an instruction from the second control unit 18, and controls the first transport mechanism 140 and the second transport mechanism 141 according to the set mode.

In the first mode, the moving unit 102 causes the first transport mechanism 140 to start storing a plurality of racks R from the first end 130*a* of the table 130. The first area P1 shown in FIG. 3 indicates an area where three racks R are stored on the front side of the table 130. The first area P1 extends to the rear of the table 130 from the first end 130*a* to a position at which the three racks R are to be stored. As the number of racks R increase, the area in which the racks R are stored extends to the rear side of the table 130. When 25 racks R are stored in the table 130, the racks R are stored in all areas of the table 130 from the first end 130*a* to the second end 130*b*.

In the second mode, the moving unit 102 causes the first transport mechanism 140 and the second transport mechanism 141 to start storing a plurality of racks R from the second end 130*b* of the table 130. The second area P2 shown in FIG. 3 indicates an area where three racks R are stored on the rear side of the table 130. The second area P2 extends from the second end 130*b* to the front side of the table 130 at a position where the three racks R can be stored. As the number of racks R increase, the area in which the racks R are accommodated extends to the front side of the table 130. When 25 racks R are stored in the table 130, the racks R are stored in all areas of the table 130 from the second end 130*b* to the first end 130*a*.

Figure 5:
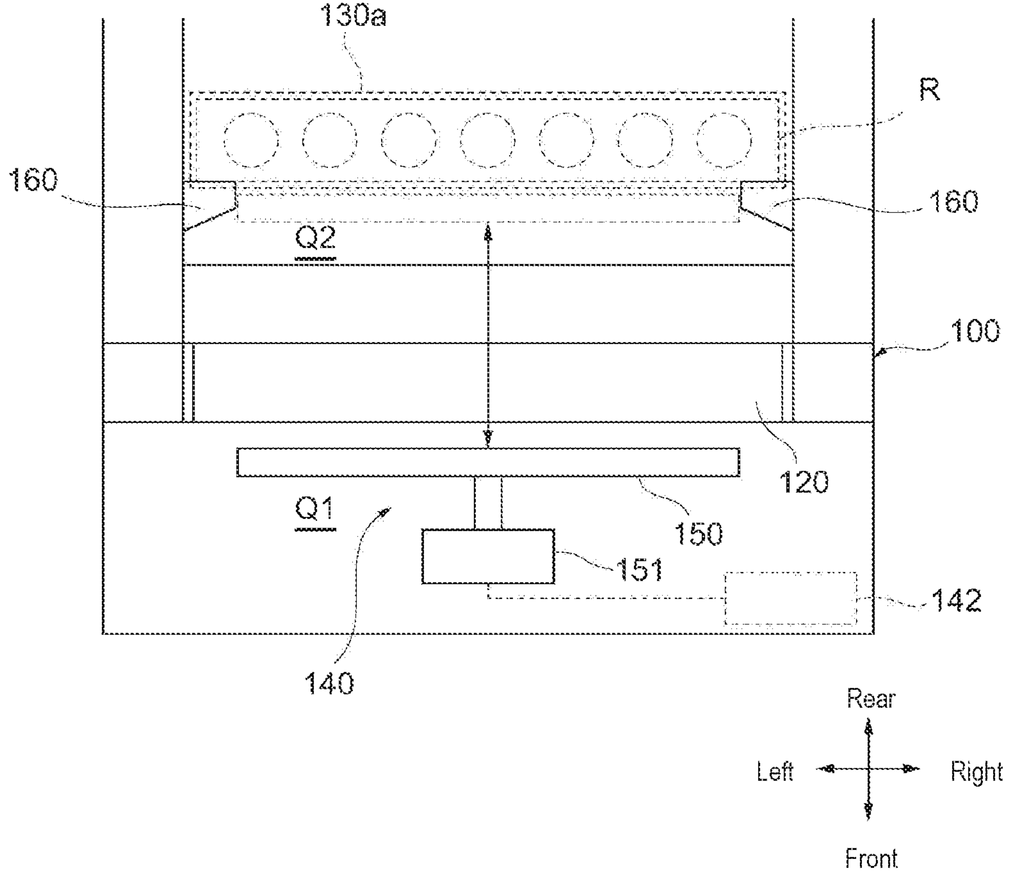
FIG. 5 is an explanatory diagram showing a structural example of a first transport mechanism.

FIG. 5 is a plan view showing a state in which the first transport mechanism 140 is removed and exposed from the storage units 15 and 16. The first transport mechanism 140 includes a flat push member 150 that is long in the left-right direction, and a driving unit 151 that moves the push member 150 in the front-rear direction. The drive unit 151 is configured to convert the rotation of the motor into the forward and backward movement of the push member 150 via a gear. The push member 150 is disposed with the position Q1 on the front side of the loading unit 100 as an initial position. The drive of the drive unit 151 is controlled by the control unit 142. The first transport mechanism 140 moves the push member 150 from the preset initial position Q1 to a position Q2 which is a predetermined distance away from the preset initial position Q1 by the driving unit 151 controlled by the control unit 142 such that the rack R can be pushed to the first end 130*a* by the push member 150.

Figure 6:
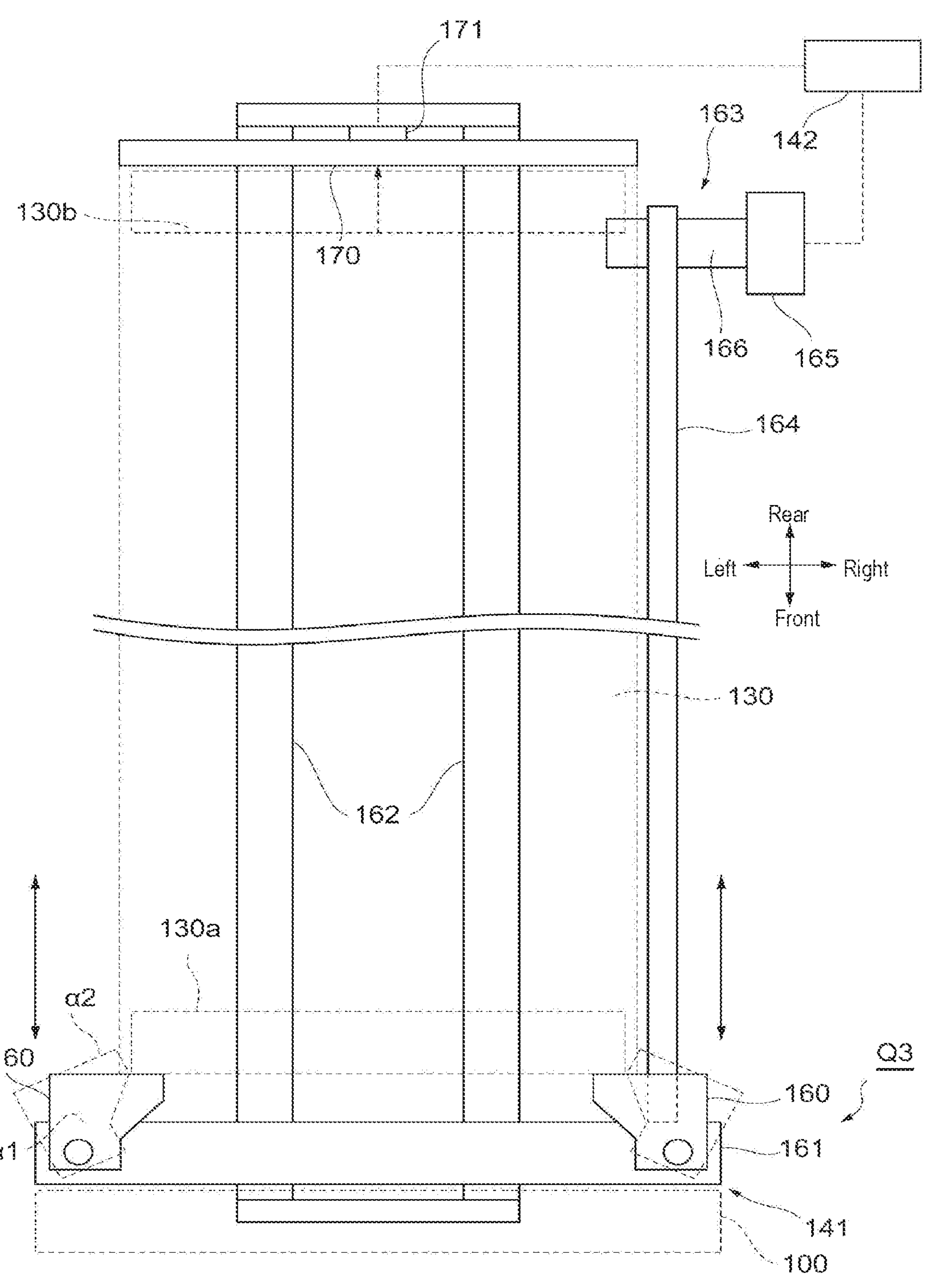
FIG. 6 is an explanatory diagram showing a structural example of a second transport mechanism.

FIG. 6 is a plan view showing the second transport mechanism 141 in a state in which the table 130 is removed and exposed from the storage units 15 and 16. The second transport mechanism 141 includes two push members 160 disposed on both sides of the table 130 in the left-right direction, a slider 161 supporting the two push members 160, a rail 162 provided with a length in the front-rear direction over both ends 130*a* and 130*b* of the table 130, and a driving mechanism 163 for moving the slider 161 in the front-rear direction along the rail 162. The push member 160 is arranged with a position Q3 behind the loading unit 100 and forward of the first end 130*a* as an initial position. The driving mechanism 163 includes a belt 164 spanning both ends 130*a* and 130*b* of the table 130, and a driving unit 165 that rotates the belt 164. The slider 161 is attached to the belt 164 so as to move in the front-rear direction by the rotation of the belt 164. The drive of the driving unit 165 is controlled by the control unit 142. The second transport mechanism 141 can move the push member 160 fixed to the slider 161 via the belt 164 in the front-rear direction via the driving unit 165 controlled by the control unit 142. The second transport mechanism 141 moves the push member 160 from the initial position Q3 to a position immediately in front of the wall 170 on the second end 130*b* side through the first end 130*a* of the table 130, so that the rack R loaded at the first end 130*a* can be moved toward the second end 130*b*. Each of the two push members 160 can transition between an initial state α1 and a retracted state α2, and is configured to return from the retracted state α2 to the initial state α1 by a spring. When the rack R moves from the loading unit 100 to the first end 130*a*, the push member 160 is pushed by the rack R and rotationally moves from the initial state α1 to the retracted state α2 to retreat from the track of the rack R. Then, when the rack R reaches the first end 130*a*, the rack R returns from the retracted state α2 to the initial state α1, and the rack R can be transported rearward.

The second transport mechanism 141 also includes a sensor 171 for detecting the presence or absence of pressure on the wall 170 on the second end 130*b* side. The sensor 171 detects the pressure when the wall 170 on the second end 130*b* side moves rearward. Information detected by the sensor 171 is output to the control unit 142, and the control unit 142 can stop the movement of the push member 160 by stopping the driving unit 165 based on the information. Therefore, the second transport mechanism 141 can move the rack Ron the table 130 rearward by the push member 160, and continue to move the rack R until the sensor 170 detects the pressure.

Figure 7:
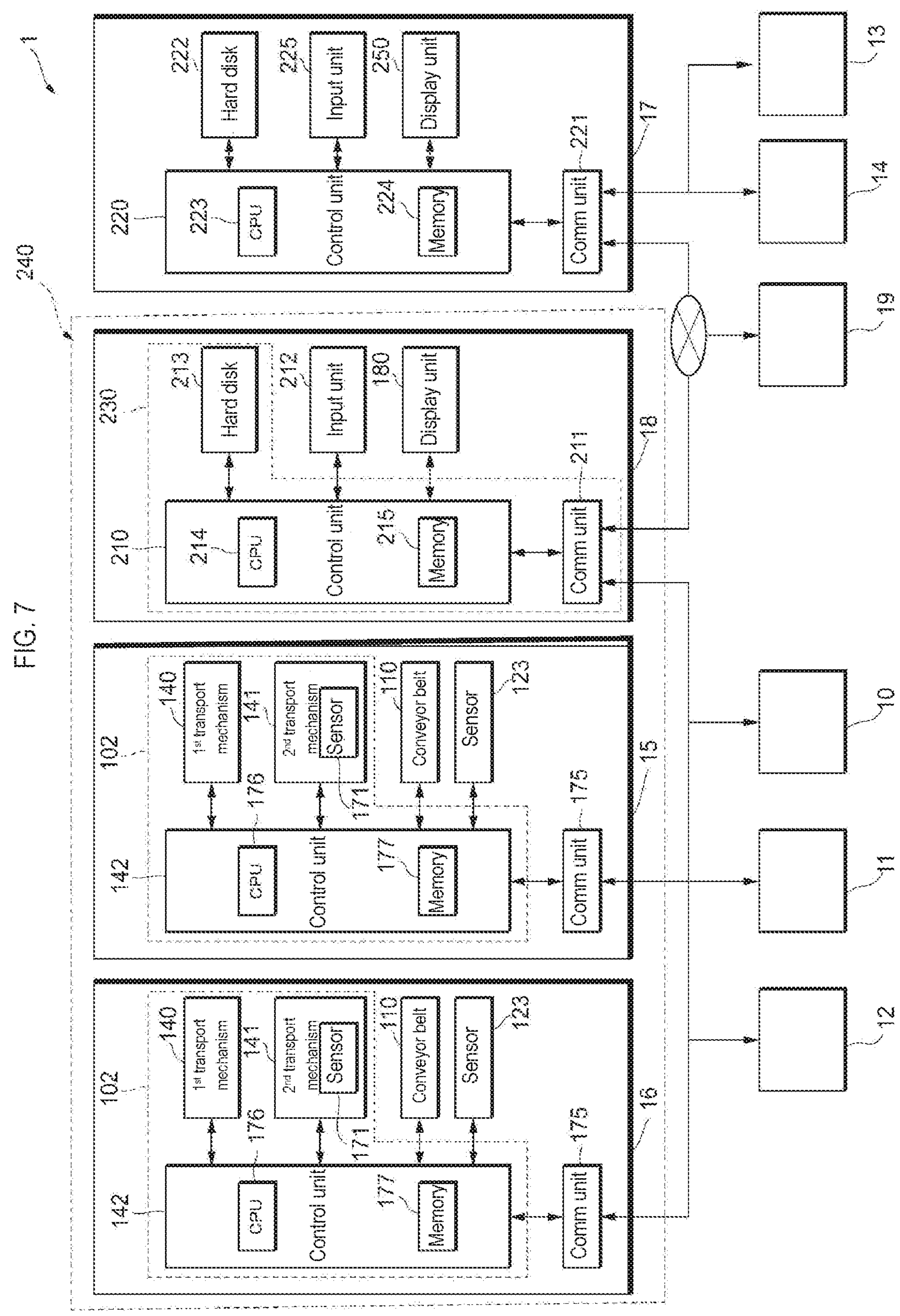
FIG. 7 is a block diagram of the testing system 1.

FIG. 7 is a block diagram showing a structure related to the control of each unit configuring the testing system 1. The storage unit 15 includes a communication unit 175 in addition to the control unit 142, the belt conveyor 110, the sensor 123, the first transport mechanism 140, and the second transport mechanism 141. The communication unit 175 is configured to be able to communicate with the second control unit 18. The control unit 142, the first transport mechanism 140, and the second transport mechanism 141 configure the moving unit 102. The control unit 142 includes a CPU 176 and a memory 177; the CPU 176 executes a program stored in the memory 177, so that the rack R can be stored in the storage unit 15. The memory 177 includes a storage medium such as a ROM, a RAM, and a memory card, and stores a program for executing a process of storing the rack R, as well as an execution file of the program and data formed by executing the program, as well as data such as setting information acquired from the second control unit 18 via the communication unit 175.

The first control unit 17 includes a control unit 220, a communication unit 221, a hard disk 222, an input unit 225, and a display unit 250. The communication unit 221 is configured to be able to communicate with the testing units 13 and 14. The communication unit 221 is configured to be able to communicate with the second control unit 18 and the host computer 19 via the network N. The hard disk 222 stores programs for executing various processes, and various data. The control unit 220 includes a CPU 223 and a memory 224, and executes various programs by reading a program stored in the hard disk 222 by the CPU 223, and developing the program in the memory 224. The memory 224 stores an execution file of the program, data formed by executing the program, and data obtained from the external testing units 13 and 14, the host computer 19, and the second control unit 18 via the communication unit 221. The control unit 220 acquires the sample ID of the sample to be tested by the testing units 13 and 14 by executing the program, and queries the host computer 19 regarding the measurement order. The control unit 220 performs an analysis based on the measurement results performed by the testing units 13 and 14, and transmits the analysis results to the host computer 19. The measurement order means a measurement item registered in advance in association with the sample ID.

The second control unit 18 includes a control unit 210, a communication unit 211, a hard disk 213, an input unit 212, and a display unit 180. The communication unit 211 can communicate with the loading units 10 and 11, the transport unit 12, the storage units 15 and 16, and the first control unit 17. The communication unit 211 also can communicate with the first control unit 17 and the host computer 19 via the network N. The hard disk 213 stores programs for executing various processes and various setting information. The control unit 210 includes a CPU 214 and a memory 215, and executes a program by reading the program stored in the hard disk 213 by the CPU 214, and developing the program in the memory 215. The memory 215 stores an execution file of the program, data produced by executing the program, and data obtained from the external loading units 10 and 11, the transport unit 12, the storage units 15 and 16, the first control unit 17, and the host computer 19 via the communication unit 211. By executing the program, the control unit 210 acquires signals of the detected passage of the rack R at a predetermined position from each of the loading units 10, 11, the transport unit 12, and the storage units 15 and 16 via the communication unit 211, and sends and receives signals between each of the units so as to indicate the transport destination of the rack R.

The control unit 210 of the second control unit 18 configures a setting unit 230 together with the communication unit 211 and the hard disk 213. The setting unit 230 realizes a function of setting a first mode and a second mode in the storage units 15 and 16; the mode setting process is performed when the testing system 1 is in a state in which various settings can be changed.

Figure 8:
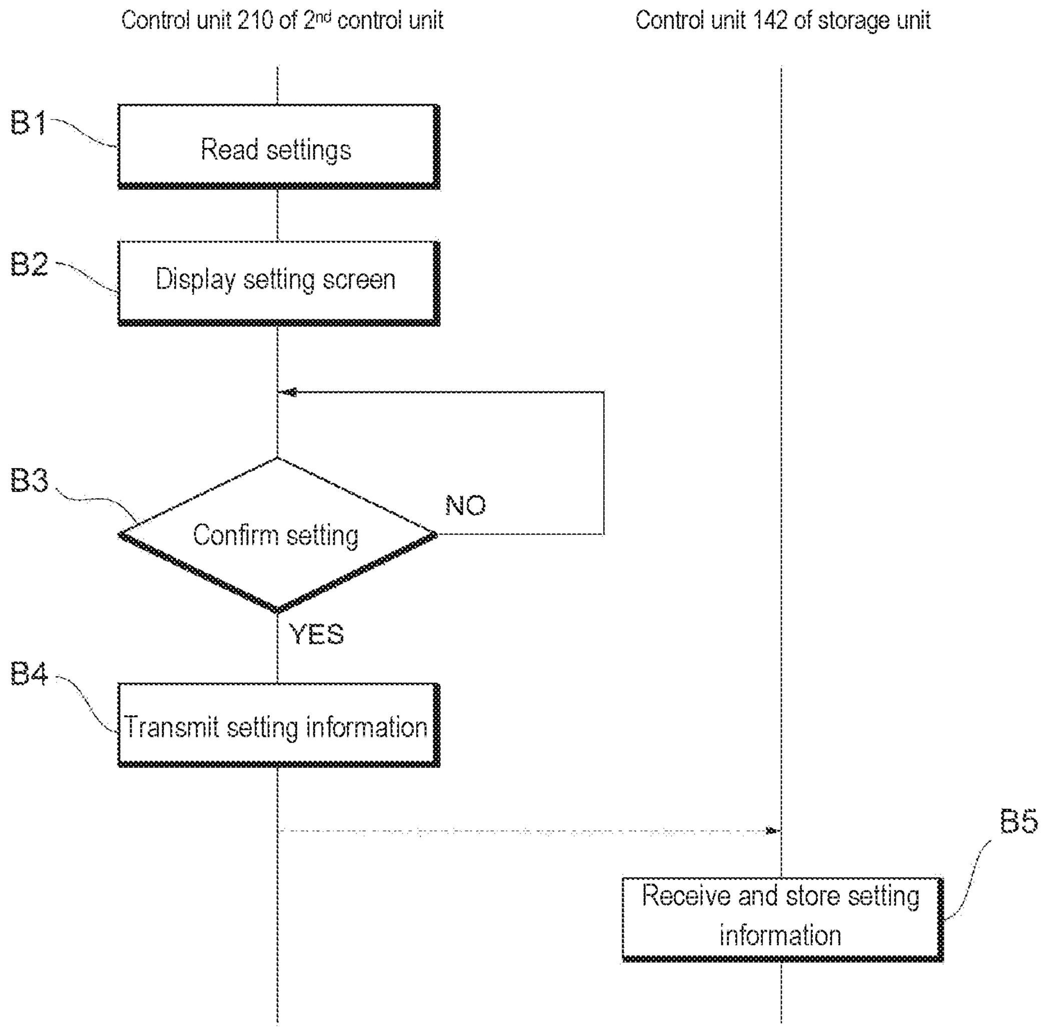
FIG. 8 is a flowchart of a mode setting process.

FIG. 8 is a flowchart showing a mode setting process performed by the control unit 210 included in the setting unit 230. Hereinafter, description will be made with reference to the reference numerals shown in FIG. 7, In the mode setting process, the control unit 210 first reads from the hard disk 213 the setting information on the mode set immediately before (step B1). Next, control unit 210 causes display unit 180 to display a setting screen for setting a mode (step B2). This setting screen is a screen corresponding to the read setting information. Then, when the control unit 210 receives an operation input to the setting screen through the input unit 212 and the next mode is determined (step B3: YES), mode setting information is generated and transmitted to the storage unit 15 and the storage unit 16 (step B4) via the communication unit 211. In this way the control units 142 of the accommodation units 15 and 16 store the received setting information in the memory 177 (step B5), and thereafter perform operations in a mode corresponding to the setting information. The mode set for the storage unit 15 and the mode set for the storage unit 16 may be the same or different.

Figure 9B:
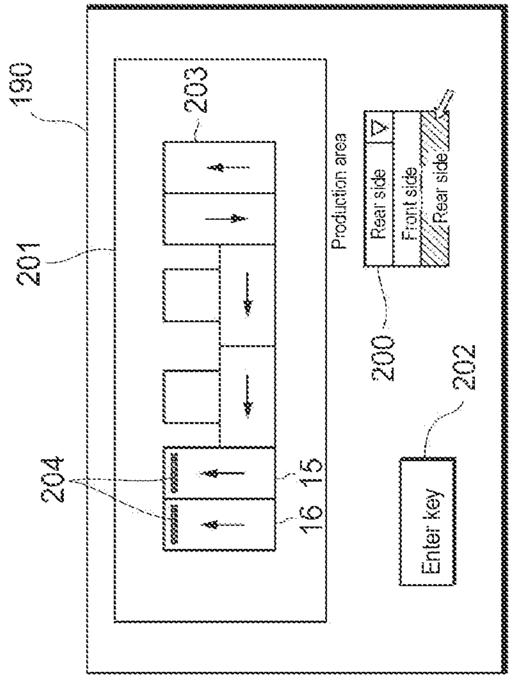
FIG. 9B is a diagram showing a setting screen when setting a second mode.
Figure 9A:
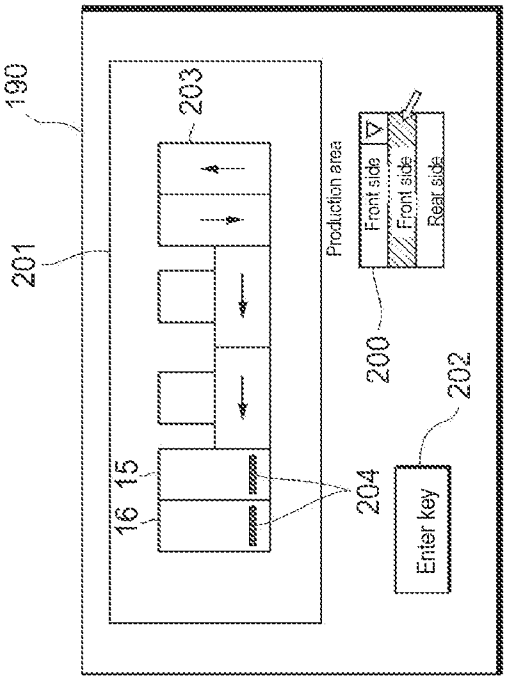
FIG. 9A is an explanatory diagram showing an example of a display of a setting screen when setting a first mode.

The setting screens 190 shown in FIGS. 9A and 9B are displayed on the display unit 180 in the above-described mode setting process, and the mode of the storage units 15 and 16 is determined by an input operation performed by the input unit 212 corresponding to the setting screen 190. The setting screen 190 includes a selection item 200 for selecting a mode to be set, a display item 201 for displaying a unit layout 203 of the testing system, and an enter button 202 for accepting an operation for confirming the mode. The selection item 200 is a field for displaying a pull-down menu and the like for receiving a selection operation to select either to start storage of the rack R from the first end 130*a* on the front side of the table 130 by setting a first mode, or to start storage of the rack R from the second end 130*b* on the rear side of the table 130 by setting a second mode. The enter button 202 is a field for accepting a decision operation for confirming the selection in the selection item 200. An object 204 changes display position in conjunction with the selection of the selection item 200 is displayed on the unit layout 203 of the display item 201.

When the operator selects "front side" from the pull-down menu of the selection item 200 as shown in FIG. 9A, the object 204 is displayed at the corresponding front side position on the collection units 15 and 16 of the unit layout 203. Next, when the operator operates the operation item 202, it is determined that the first mode is selected as the mode corresponding to the selection in the selection item 200, and the corresponding setting information is transmitted from the second control unit 18 to the storage unit 15 and 16. In this way the storage units 15 and 16 operate in the first mode corresponding to the received setting information. On the other hand, when the operator selects "rear side" from the pull-down menu of the selection item 200 as shown in FIG. 9B, the object 204 is displayed at the corresponding rear side position on the collection units 15 and 16 of the unit layout 203. Next, when the operator operates the operation item 202, it is determined that the second mode is selected as the mode corresponding to the selection in the selection item 200, and the corresponding setting information is transmitted from the second control unit 18 to the storage unit 15 and 16. In this way the storage units 15 and 16 operate in the second mode corresponding to the received setting information. The mode of the storage units 15 and 16 is selected using the setting screen 190 in this way.

When the first mode is set by the above-described mode setting, storage of a plurality of racks R is started from the first end 130*a* in the housing units 15 and 16 shown in FIG. 3. As the number of racks R increases, the racks R are stored from the first end 130*a* of the table 130 to the rear side. When the second mode is set, storage of the plurality of racks R is started from the second end 130*h* in the storage units 15 and 16. As the number of racks R increases, the racks R are stored from the second end 130*b* of the table 130 to the front side.

Figure 10:
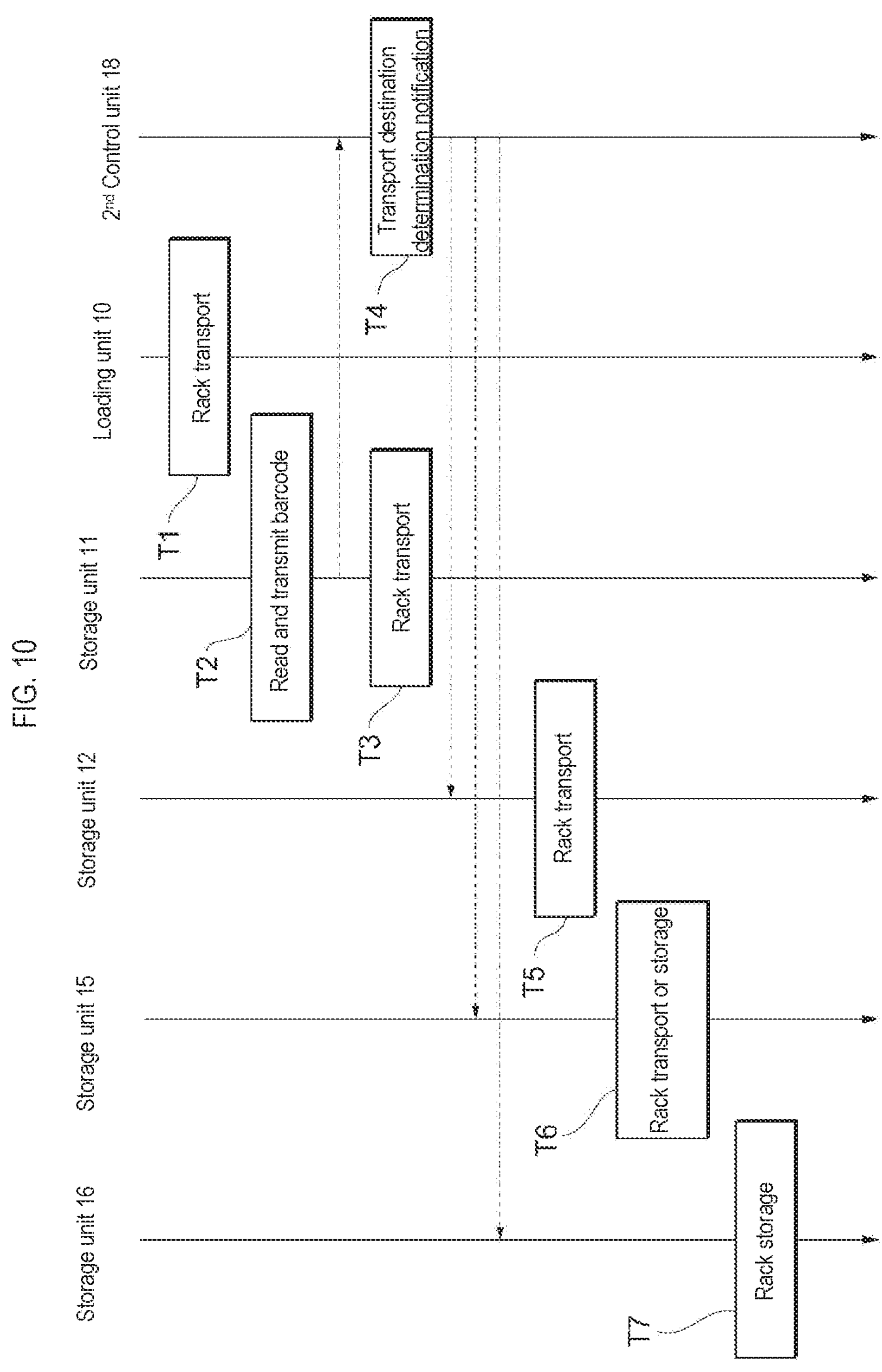
FIG. 10 is a flowchart showing the main processing in each unit configuring the testing system.

Next, main processing of each unit from loading to storage of the rack R in the testing system 1 configured as described above will be described. FIG. 10 is a flowchart showing main processing performed by the loading units 10 and 11, the transport unit 12, the storage units 15 and 16, and the second control unit 18. Hereinafter, description will be made with reference to the reference numerals shown in FIGS. 1, 3, 7, and 9.

When a rack R holding a plurality of containers A containing untested samples is to be loaded, the loading unit 10 transports the rack R rearward, moves the rack R to the left at the rear end to the loading unit 11 (step T1). The loading unit 11 reads the barcodes BC1 and BC2 of the rack R and the container A sent from the loading unit 10 via the rack information reading unit 21 to acquire the identification information of the rack R and the identification information of the container A, and, the identification information of the rack R and the identification information of the container A are transmitted to the second control unit 18 (step T2). The loading unit 11 also transports the rack R forward from the rearmost part, so that the rack R is moved to the left at the foremost part to advance the rack R to the transport unit 12 (step T3). The control unit 220 of the second control unit 18 determines the transport destination of the rack R based on the received information, and notifies the transport unit 12 and the storage units 15 and 16 (step T4). At this time, the control unit 220 of the second control unit 18 may determine the transport destination of the rack R to control the racks so that the testing load in the two testing units 13 and 14 is distributed and the number of racks accommodated in the two storage units 15 and 16 is dispersed. The transport unit 12 sends the rack R from the main transport path 51 to the testing path 53 based on the information relating to the transport destination of the rack R received from the second control unit 18, and sends the rack R to either the testing unit 13 or the testing unit 14; alternatively, a rack R that has been transported to both and has been tested by the testing units 13 and 14 is then transported from the testing path 53 to the main transport path 51 and sent to the storage unit 15 (step T5). The storage unit 15 stores the rack in the table 130 or transports the rack R to the storage unit 16 based on the information on the transport destination of the rack R received from the second control unit 18 (step T6). The storage unit 16 stores the rack R sent from the storage unit 15 on the table 130 (step T7).

Figure 11:
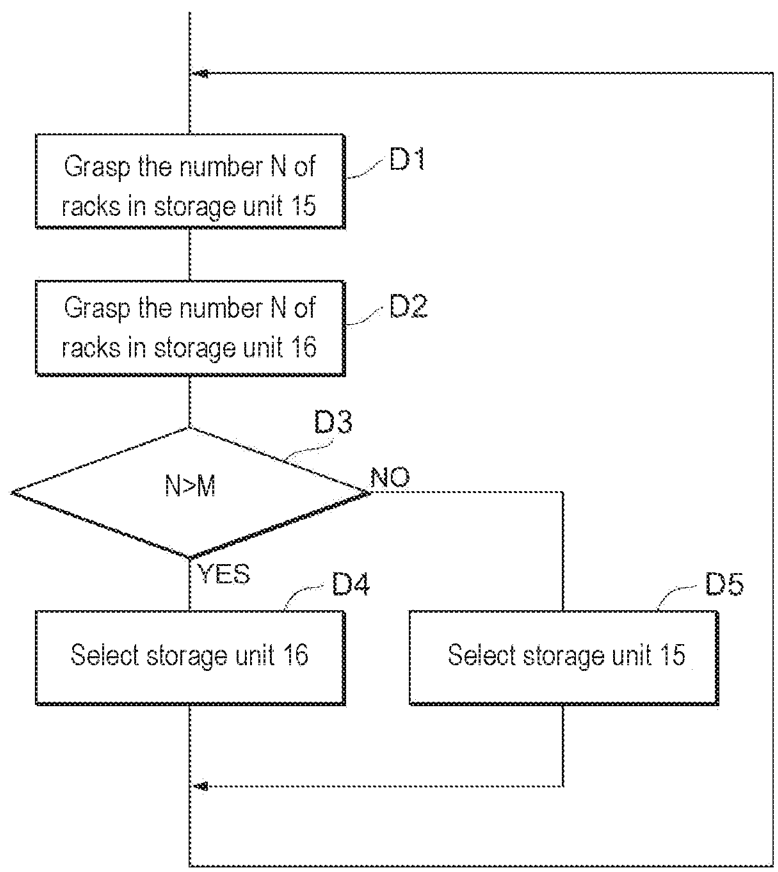
FIG. 11 is a flowchart of a process of selecting a storage unit for storing a rack in the second control unit.

When the second control unit 18 determines which of the storage units 15 and 16 is the destination of the rack R (step T4), the processing flow shown in FIG. 11 can be used. FIG. 11 is a flowchart of a selection process in the second control unit 18 for selecting which of the storage units 15 and 16 stores the rack. The control unit 210 of the second control unit 18 grasps the number N of racks stored in the storage unit 15 (step D1), and grasps the number M of racks R stored in the storage unit 16 (step D2). Then, the second control unit 18 compares the storage number N with the storage number M (step D3), and when the storage number N is larger than the storage number M, the storage unit 16 is set as the storage destination of the next rack R (step D4), whereas when the storage number N is smaller than the storage number M, the storage unit 15 is selected as the storage destination of the next rack R (step D5). In this way the number of the racks R stored in the storage units 15 and 16 can be dispersed.

Figure 12:
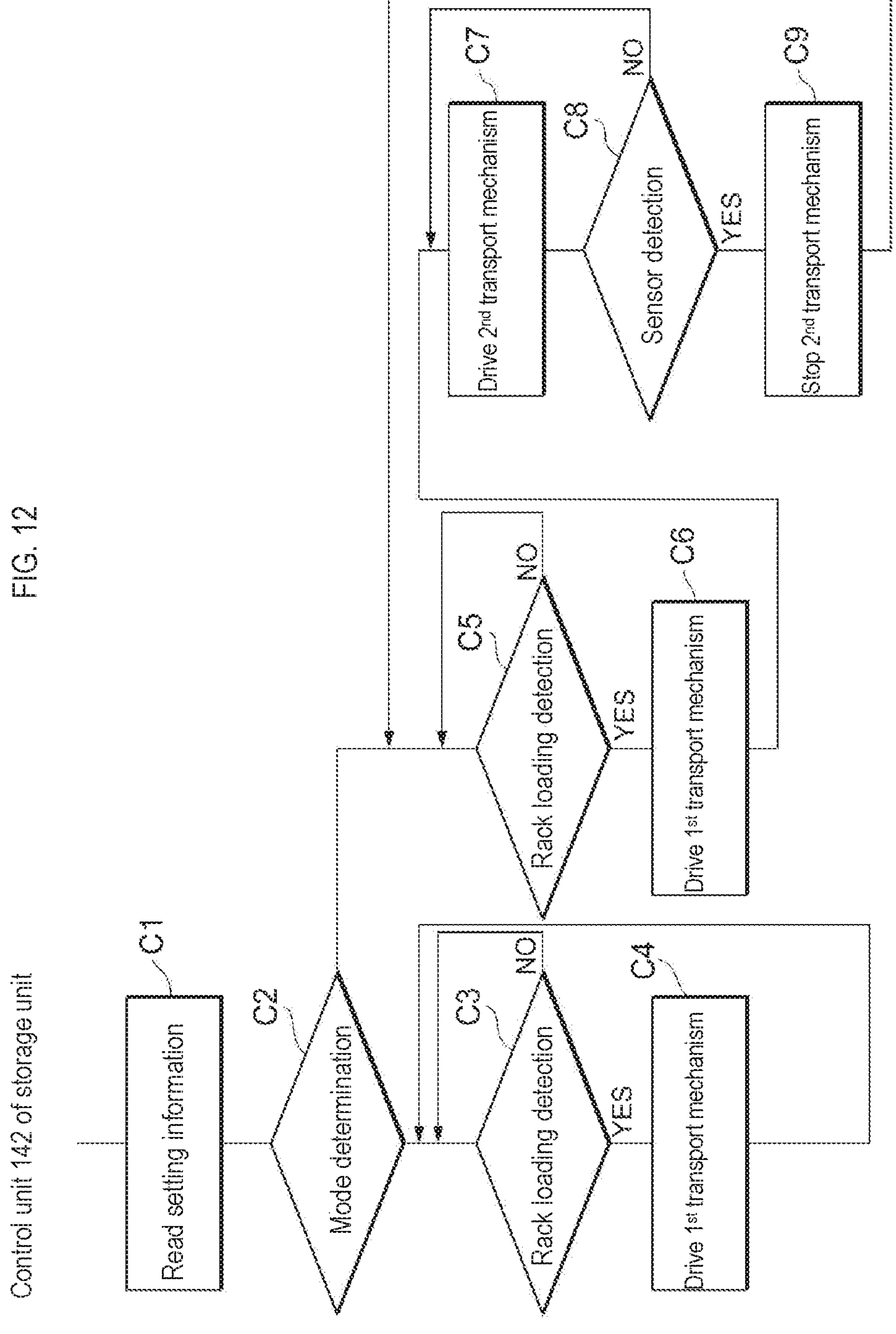
FIG. 12 is a flowchart showing a process of storing a rack in a storage unit.

FIG. 12 shows a flow of a rack R storage process performed by the storage units 15 and 16. The control unit 142 of the storage units 15 and 16 reads the setting information related to the mode stored in the memory 177 (step C1), and either determines the first mode or the second mode in accordance with the read setting information (step C2).

When the control unit 142 of the storage units 15 and 16 determines that the first mode is to be set and the sensor 123 of the loading unit 100 detects that the rack R is loaded into the loading unit 100 (step C3: YES), the first transport mechanism 140 is driven to transfer the rack R of the loading unit 100 to the first end 130*a* (step C4). The control unit 142 repeats the transfer of a rack R to the first end 130*a* each time the loading of a rack R into the loading unit 100 is detected. Since the first transport mechanism 140 sequentially moves the racks R to the first end 130*a* to the front direction of the table 130 by the push member 150 through this process, a maximum of 25 racks R can be stored by starting the storage of a plurality of racks R from the first end 130*a*.

When the control unit 142 of the storage units 15 and 16 determines that the second mode is to be set and the sensor 123 of the loading unit 100 detects that a rack. R is loaded into the loading unit 100 (step C5: YES), the first transport mechanism 140 is driven to transport the rack R. of the loading unit 100 to the first end 130*a* (step C6), and then the second transport mechanism 141 is driven to move the rack R to the second end 130*b* (step C7). Then, when the sensor 171 of the second transport mechanism 141 detects the pressure when the wall 170 adjacent to the second end 130*b* is pushed by the rack R (step C8: YES), the control unit 142 stops the drive of the second transport mechanism 141 (step C9).

The control unit 142 repeats transporting the rack R by the first transport mechanism 140 and the second transport mechanism 141 each time the loading of the rack R into the loading unit 100 is detected. The second transport mechanism 141 moves the rack R to the rear of the table 130 by the push member 160 until the rack R abuts the wall 170 on the second end 130*b* side, or has already moved to the second end 130*b* side, or moves the rack R until the rack R contacts a rack R (previous rack R) already stored on the second end 130*b* side and the sensor 171 responds to a rack R pushing against the wall 170. In this way storage of a plurality of racks R is started from the second end 130*b*, and up to 25 racks R can be stored.

Figures 13A, 13B, 13C, 13D, 13E, 13F, 13G, 13H:
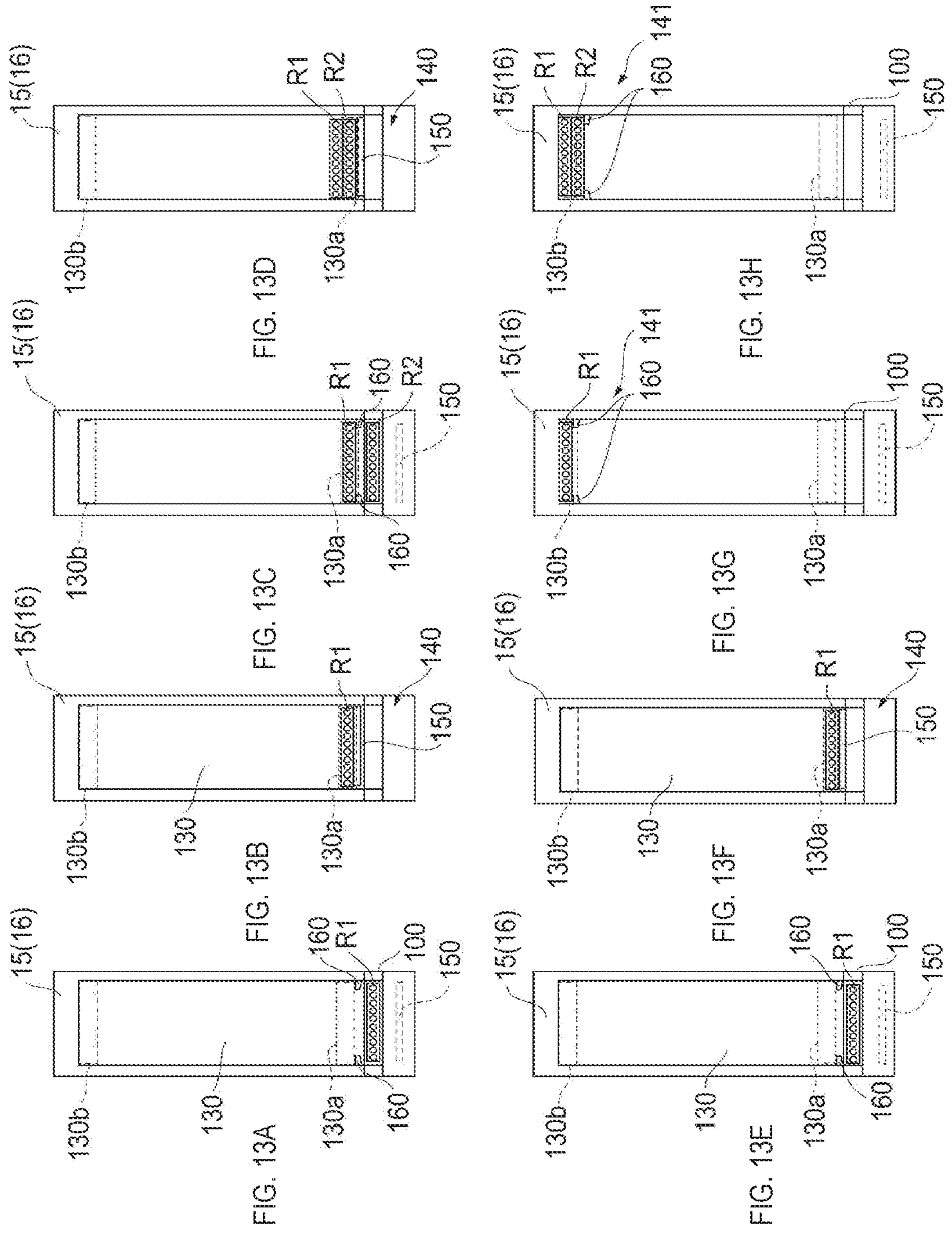
FIGS. 13A, 13B, 13C, and 13D are plan views showing rack storage state in a storage unit in a first mode; 13E, 13F, 13G, and 13H are plan views showing the rack storage state in a second mode in the storage unit.

FIGS. 13A, 13B, 13C, and 13D are plan views schematically showing a change in the storage state of the rack R in the first mode in the storage units 15 and 16. In the first mode, a rack R1 first loaded into the loading unit 100 of the storage units 15 and 16 as shown in FIG. 13A is transported to the first end 130*a* of the table 130 by the push member 150 of the first transport mechanism 140 as shown in FIG. 13B. Next, as shown in FIG. 13C, the next rack R2 that has been loaded into the loading unit 100 is pushed by the push member 150 of the first transport mechanism 140 to the front end 130*a* of the table 130 as shown in FIG. 13D. In this way a previously transported rack R1 is pushed by the rack R2, and moves to the rear position adjacent to the rack R1 in the first area P1. The plurality of racks R thus loaded into the loading unit 100 are transported to the first end 130*a* by the push member 150 of the first transport mechanism 140, and push the existing rack R on the table 130 rearward. In this way the storage of the plurality of racks R starts from the first end 130*a*, such that the racks R are sequentially moved to the first end 130*a*, and are gathered and stored in rearward from the first end 130*a* of the table 130. Therefore, when a worker W shown in FIG. 1 predominantly performs work in the work area S1 to the front of the storage units 15 and 16 and, for example, performs the operation of removing five racks R from the storage units 15 and 16 with the timing at which the five racks R are being stored in the storage units 15 and 16, respectively, the worker W can remove the five racks R from the front side of the housing units 15 and 16 and achieve good workability.

FIGS. 13E, 13F, 13G, and 13H are plan views schematically showing changes in the storage state of the racks R in the storage units 15 and 16 in the second mode. In the second mode shown in FIG. 13E, a rack R1 which has been first loaded into the loading unit 100 of the storage units 15 and 16 is moved by the push member 150 of the first transport mechanism 140 to the first end 130*a* of the table 130 as shown in FIG. 13F, and then transported to the second end 130*b* of the table 130 by the push member 160 of the second transport mechanism 141 as shown in FIG. 13G. At this time, the sensor 171 of the second transport mechanism 141 detects that the wall 170 has been pressed by the rack R1, and the detection triggers the movement of the push member 160 to stop, whereupon the transport of the rack R1 stops. Next, the rack R2 loaded into the loading unit 100 is transported rearward on the table 130 by the push member 150 of the first transport mechanism 140 and the push member 160 of the second transport mechanism 141 so as to move forward one rack from the second end 130*b*, as shown in FIG. 13H. At this time, since the rack R1 and the wall 170 are pushed by the rack R2, and this is detected by the sensor 171 whereupon the movement of the pushing member 160 is stopped, and the transport of the rack R2 is stopped. The storage of plurality of racks R loaded into the loading unit 100 in this manner are stored starting from the second end 130*b* of the table 130 by the push member 150 of the first transport mechanism 140 and the push member 160 of the second transport mechanism 141 so as to be sequentially moved to the side of the second end 130*b* of the table 130, and sequentially stored toward the front from the second end 130*b* of the table 130. Therefore, when the worker W shown in FIG. 1 predominantly performs work in the work area S2 to the rear of the storage units 15 and 16 and, for example, performs the operation of removing five racks R from the storage units 15 and 16 with a timing at which the five racks R are being stored in the storage units 15 and 16, respectively, the worker W can remove the five racks R from the rear side of the storage units 15 and 16 and achieve good workability.

According to the present embodiment described above, the position at which the storage of the rack R is started can be switched to the front side or the rear side according to the mode of the storage units 15 and 16 by setting the mode via the setting unit 230 shown in FIG. 7. Hence, the worker W can remove the rack R from the table 130 more easily since it is possible to set the mode so that the rack R starts storage from a position closer to the work area S of the worker W.

As shown in FIG. 3, since the first end 130*a* and the second end 130*b* are in the same horizontal plane area, it is unnecessary to move the rack R up and down, and the first moving mechanism 140 and the second the moving mechanism 141 can be less complex in configuration. In the case of the first mode, workers who are working at the front can easily remove a rack since the first rack to be stored is stopped at the first end 130*a*, and the racks are arranged rearward (first direction) from the first end 130*a* toward the center of the table 130. Similarly, in the case of the second mode, workers who are working at the rear can easily remove a rack since the first rack to be stored is stopped at the second end 130*b*, and the racks are arranged forward (second direction) from the second end 130*b* toward the center of the table 130. In this way the work of the worker W removing the rack R from the table 130 can be effectively simplified.

A rack R can be suitably moved to the table 130 by the moving unit 102 while having a simple configuration since the moving unit 102 includes a first transport mechanism 140 for moving a rack R of the loading unit 100 to the table 130, and a second transport mechanism 141 for moving a rack Ron the table 130.

The first transport mechanism 140 is configured to move the rack R of the loading unit 100 to a first end 130*a* of the table 130 by moving the rack R in a predetermined direction by a prescribed distance. In this way the movement of the rack R to the table 130 can be performed with a simple control since it is not necessary to control the moving distance of the individual rack R.

The second transport mechanism 141 is configured to move the rack R on the table 130 until the rack R strikes the wall 170 of the second end 130*b* of the table 130, or strikes another previously stored rack R on the second end 130*b* side. In this way the movement of the racks R to the table 130 can be performed with simple controls since it is not necessary to manage the positions of the individual racks R in the memory.

The storage units 15 and 16 include a sensor 171 that detects pressure on the wall 170 of the second end 130*h* of the table 130. In this way the movement of the rack R can be easily controlled since the rack R on the table 130 moves until it strikes a wall 170 of the second end 130*b* of the table 130, or strikes another previously stored rack R on the second end 130*b* side which is detected by the sensor 171.

As shown in FIGS. 9A and 9B, the testing system 1 includes a display unit 180 that displays a setting screen 190 for setting a position at which the rack R starts to be stored; the setting unit 230 changes the position of starting to store the rack Ron the table 130 of the second moving unit 102 based on the setting in the setting screen 190 of the display unit 180. In this way the position at which the worker W starts to store the rack R on the table 130 can be suitably performed.

The setting screen 190 includes a selection item 200 for selecting a position at which the storage of the rack R is started. In this way it is possible for a worker W to suitably select the position at which to start to store the rack R.

The display of the display item 201 changes in conjunction with the selection in the selection item 200. In this way it easier to understand the rack collection and storage area of the layout 203 of the storage device 240 displayed on the setting screen 190.

As shown in FIG. 1, the testing system 1 includes a loading unit 10, testing units 13 and 14, a storage device 240, and a transport unit 12, and is configured to be able to access the containers of the rack R on the transport path. Although the testing system 1 is large and the work area S of the worker W is also likely to be large, the advantage of changing the starting position for storing the racks R to a position close to the work area of the worker W is significant since the position at which the racks R start to be stored on the table 130 can be changed by the setting unit 230 in the testing system 1. Hence, the work of removing the rack R from the table 130 by the worker W can be performed more easily.

In the testing system 1, the transport path 50 extends in the left-right direction, connects to the loading unit 100 of the storage device 240, and the table 130 extends in the front-rear direction orthogonal to the transport path 50. In this case, the work area S of the worker W is divided into the front side and the rear side of the transport path 50. In such a testing system 1, being able to change the starting position for storing the rack Ron the table 130 is greatly advantageous.

Although the preferred embodiments of the present invention have been described above with reference to the accompanying drawings, the present invention is not limited to such examples. It is clear that those skilled in the art can conceive various changes or modifications within the scope of the invention described in the claims, and it is to be understood that these changes and modifications naturally belong to the technical scope of the present invention.

For example, although the second control unit 18 shown in FIG. 7 includes the setting unit 230 in the above-described embodiment, another unit also may include the setting unit 230. For example, the storage units 15 and 16, and the first control unit 17 also may have the function of the setting unit 230, or two or more of the storage units 15 and 16, and the first control unit 17 or the second control unit 18 also may cooperatively have the function of the setting unit 230.

Figure 16:
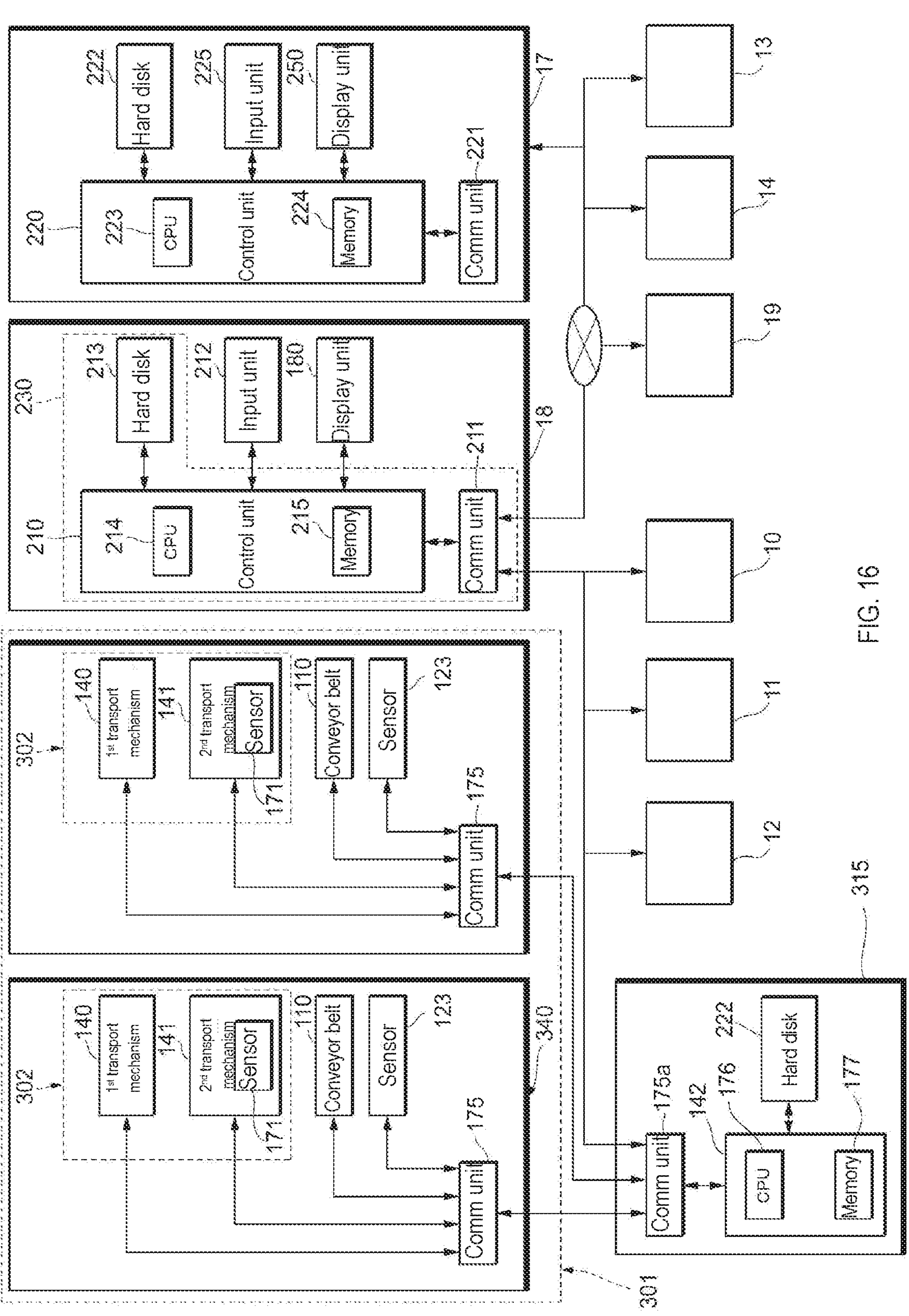
FIG. 16 is a schematic diagram showing another example of the layout of the testing system.

As shown in FIG. 7, in the above embodiment, the setting unit 230 included in the storage device 240 sets the storage mode of the sample rack in the storage device 240, and the control unit 142 of the storage unit 240 controls the first transport mechanism 140 and the second transport mechanism 141 in accordance with these settings. However, the embodiment is not limited to this configuration inasmuch as the setting unit 230 and the control unit 142 may be provided separately from the storage device 240 as shown in FIG. 16. Reference numeral 315 in FIG. 16 indicates a control unit having a separately provided control unit 142, and the control unit 315 includes a hard disk 222 and a communication unit 175*a*.

The position at which the storage of the rack Ron the table 130 shown in FIGS. 13A-13H is started is not limited to the first end 130*a* or the second end 130*b*. For example, the rack R may be configured to be stored forward from a reference position in front of the table 130. The rack R also may be configured to be stored rearward from a reference position in the rear of the table 13. The first reference position and the second reference position may be positioned differently on a different horizontal plane, that is, a configuration in which the rack R is transported in the vertical direction may be used, for example. The number of areas set as the positions at which storage of the racks R starts is not limited to two, and may be three or more.

The configurations of the storage units 15 and 16 are not limited to those in the above-described embodiment. For example, the storage unit may be configured so that a plurality of racks R are arranged in the left-right direction. The storage unit also may include a plurality of loading units, and for example, two loading units 100 may be arranged in parallel in the front-rear direction on the front side or the rear side of the storage unit. The loading unit 100 also may be provided on each of the front side and the rear side of the storage unit. One loading unit 100 also may be provided near the center of the table 12 in the front-rear direction. The configuration and operation of the moving unit 102 are not limited to those of the above-described embodiment; for example, not only the first transport mechanism 140 but also the second transport mechanism 141 may operate in the first mode. In the second mode, the rack R also may be transported only by the first transport mechanism 140.

Figure 14:
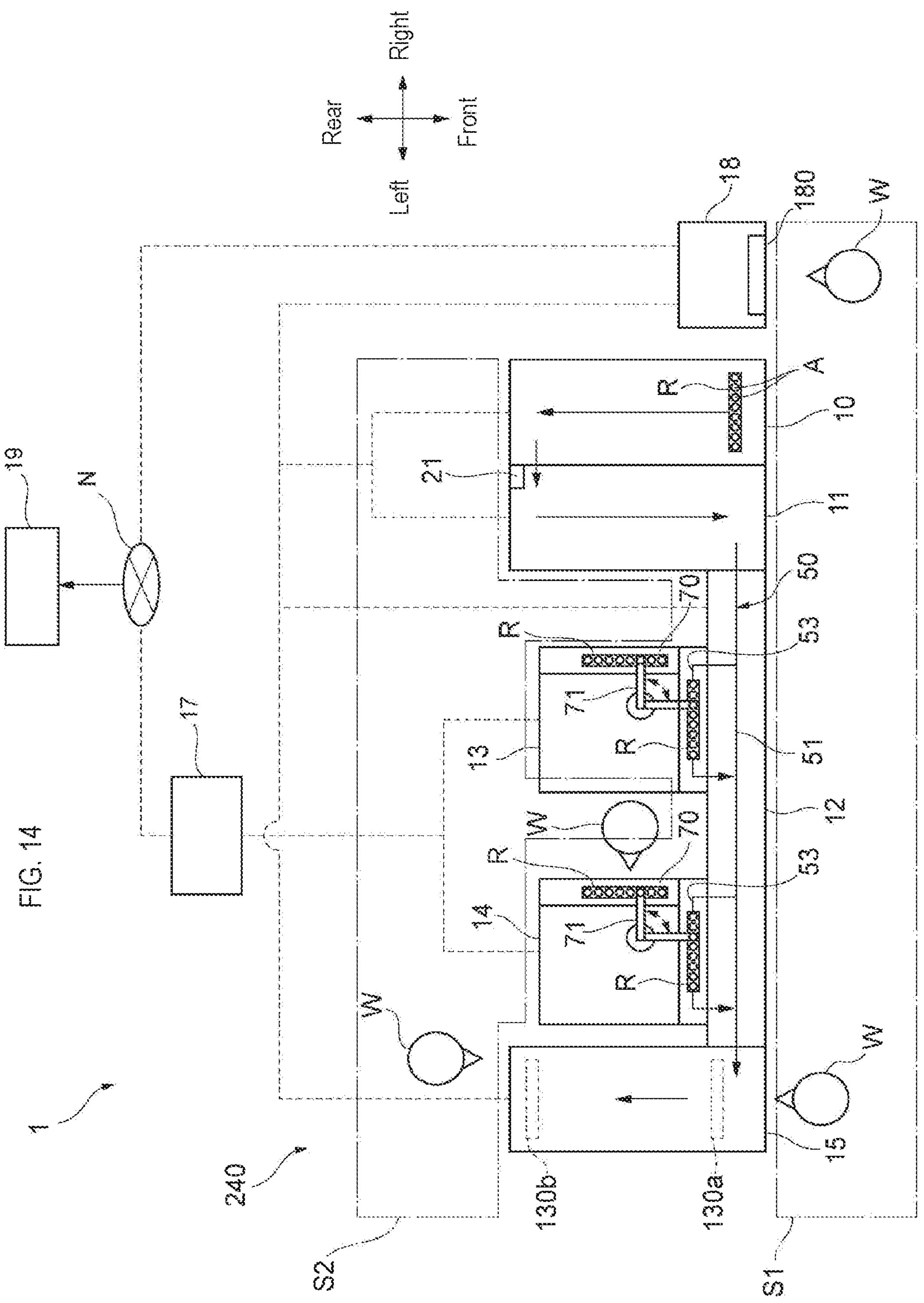
FIG. 14 is a schematic diagram showing another example of the layout of the testing system.
Figure 15:
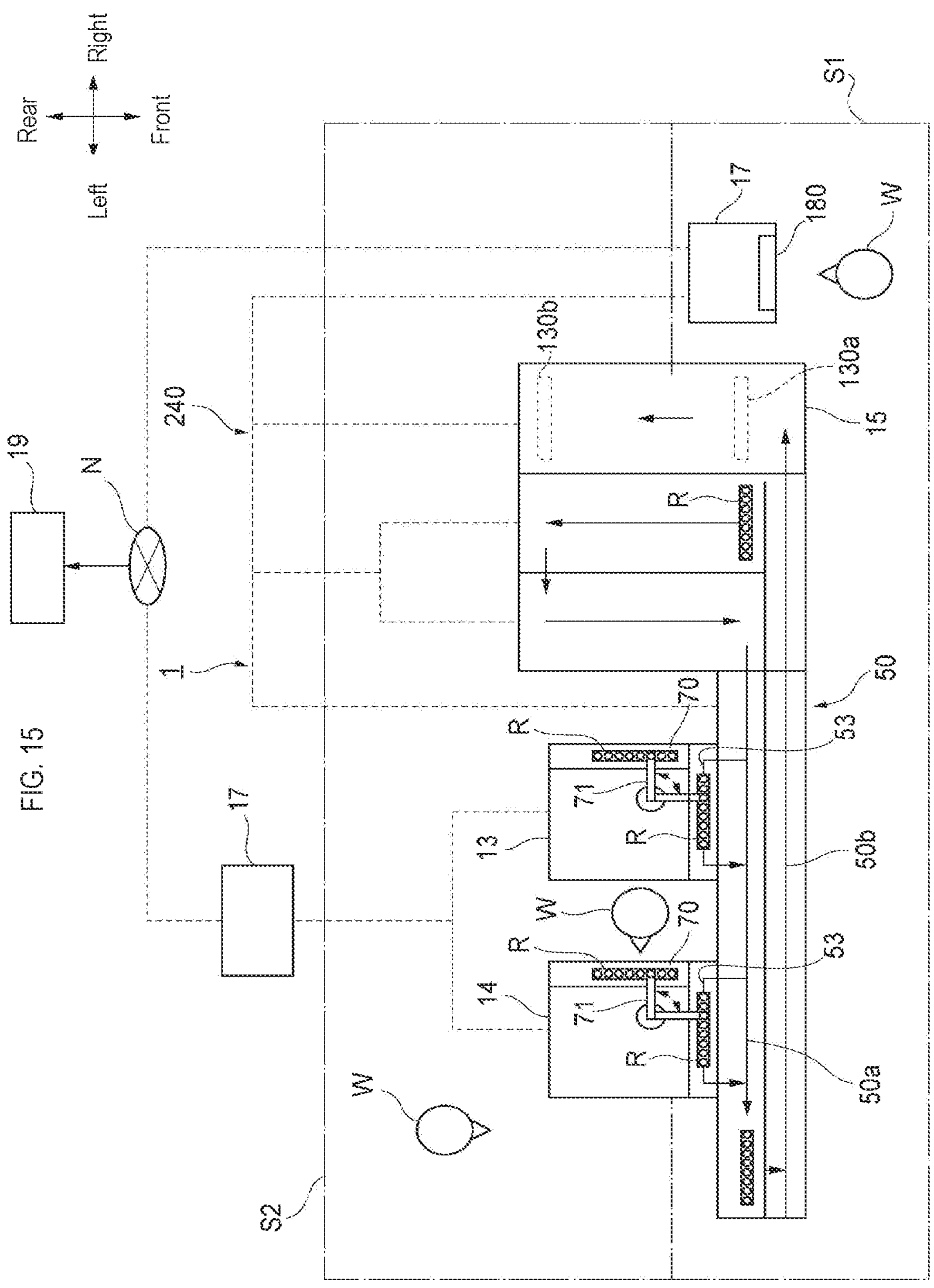
FIG. 15 is a schematic diagram showing another example of the layout of the testing system.

The structure of the testing system 1 is not limited to the above-described embodiment. For example, the unit layout of the testing system is not limited to the above example, and the numbers and positions of the storage units 15 and 16 can be appropriately changed. For example, the number of storage units 15 also may be one, as shown in FIG. 14. As shown in FIG. 15, the storage units 15 and 16 also may be provided adjacent to the loading unit 10. In this case, the transport path 50 also may include an outbound path 50*a* from the loading unit 11 (the loading unit 10 side) toward the testing units 13 and 14 side, and a return path 50*b* from the testing units 13 and 14 side toward the storage units 15 and 16 side. The structure of the transport path 50 can be appropriately changed according to the unit layout of the testing system 1. In the storage device and the testing system according to the present invention, types of samples and types of testing are not particularly limited.

INDUSTRIAL APPLICABILITY

The present invention is useful when providing a testing system, an storage device, and a rack storage method that can set the storage of a rack according to the situation of a facility.

What is claimed is:

1. A testing system comprising:

a testing device for testing a sample in a respective container held in a respective rack, wherein each rack has a length along which the containers held in the rack are arranged in line and a width orthogonal to the length;

a transport device for transporting the racks to the testing device and to a storage device, the storage device configured to receive racks transported by the transport device back from the testing device, wherein the storage device comprises a linear storage channel having a longitudinal length defined by a first reference end and a second reference end opposite to the first reference end, the linear storage channel being configured to receive racks transported back from the testing device and store the received racks therein so that the received racks are arranged in a stack in a direction of their widths along the longitudinal length of the linear storage channel;

a controller configured to receive a user selection of a first mode or a second mode prior to initial testing of the sample by the testing device, wherein in the first mode, the received racks are accumulated in the stack in the linear storage channel along the longitudinal length from the first reference end of the linear storage channel, and in the second mode, the received racks are accumulated in the stack in the linear storage channel along the longitudinal length from the second reference end of the linear storage channel;

push members controlled by the controller to push the received racks in the linear storage channel along the longitudinal length to store the received racks either from the first reference end of the linear storage channel or from the second reference end thereof according to a selected one of the first and second modes; and a display for displaying a setting screen for setting the first mode or the second mode, wherein the controller is configured to set the first mode or the second mode according to a selection of the first mode or the second mode by an input operation on the setting screen.

2. The testing system according to claim 1, wherein the push members comprise a first push member and a second push member, the first and second push members are controlled by the controller to push the received racks along the longitudinal length of the linear storage channel to arrange the received racks in the linear storage channel either from the first reference end of the linear storage channel or from the second reference end thereof according to a selected one of the first and second modes.

3. The testing system according to claim 2, wherein the first reference end and the second reference end of the linear storage channel are in a common horizontal plane.

4. The testing system according to claim 2, wherein in the first mode, the first push member is controlled by the controller to push a newly received rack to the first reference end of the linear storage channel to move an immediately preceding rack away from the first reference end so that accumulation of the received racks in the linear storage channel grows from the first reference end toward the second reference end in the first mode, and in the second mode, the second push member is controlled by the controller to push a newly received rack from the first reference end toward the second reference end along the longitudinal direction until the newly received rack becomes in contact with a immediately preceding rack also pushed toward the second reference end in the second mode so that accumulation of the received racks in the linear storage channel grows from the second reference end toward the first reference end in the second mode.

5. The testing system according to claim 4, wherein in the first and second modes, accumulation of the received racks in the linear storage channel grows toward a center of the linear storage channel.

6. The testing system according to claim 2, wherein the first push member is controlled by the controller to push the received racks one at a time to the first reference end of the linear storage channel; and the second push member is controlled by the controller to push the received racks one at a time through the linear storage channel toward the second reference end of the linear storage channel.

7. The testing system according to claim 6, wherein the first push member is controlled by the controller to push a newly received rack to the first reference end of the linear storage channel to move an immediately preceding rack away from the first reference end so that accumulation of the received racks in the linear storage channel grows from the first reference end toward the second reference end in the first mode.

8. The testing system according to claim 6, wherein the second push member is controlled by the controller to push a newly received rack from the first reference end toward the second reference end until the newly received rack becomes in contact with an immediately preceding rack also pushed toward the second reference end in the second mode so that accumulation of the received racks grows from the second reference end toward the first reference end in the second mode.

9. The testing system according to claim 8, further comprising a sensor for detecting presence of the rack at the second reference end of the linear storage channel.

10. The testing system according to claim 1, wherein the setting screen comprises selection items representing the first mode and the second mode, respectively; and the controller is configured to set the first mode or the second mode based on selection of one of the selection items.

11. A testing system comprising:

a testing device for testing a sample in a respective container held in a respective rack, wherein each rack has a length along which the containers are arranged in line and a width orthogonal to the length;

a transport device for transporting the racks to the testing device, and from the testing device to a storage device, wherein the storage device configured to store racks holding the container whose sample is tested by the testing device, wherein the storage device has a longitudinal length defined by a first reference end and a second reference end opposite to the first reference end, the storage device being configured to receive racks transported back from the testing device and store the received racks therein so that the received racks are arranged in a stack in a direction of their widths along the longitudinal length of the storage device;

a user interface displayed for selection of a first mode or a second mode, wherein in the first mode, the received racks are arranged in the storage device along the longitudinal length thereof from the first reference end of the storage device, and in the second mode, the received racks are arranged in the stack in the storage device along the longitudinal length thereof from the second reference end of the storage device;

a controller configured to receive a selection on the user interface of the first or second mode for each rack and set a selected one of the first or second mode prior to initial testing of the sample in the rack by the testing device; and push members controlled by the controller to push the received racks into the storage device for arrangement of the received racks in the storage device; and the controller is further configured to control the push members to arrange the received racks in the stack in the storage device along the longitudinal length thereof either from the first reference end of the storage device or from the second reference end thereof according to a set one of the first or second modes.

* * * * *